United States Patent
Fischell et al.

Patent Number: 5,695,516
Date of Patent: Dec. 9, 1997

[54] LONGITUDINALLY ELONGATING BALLOON EXPANDABLE STENT

[75] Inventors: Robert E. Fischell, Dayton, Md.; David R. Fischell, Fair Haven, N.J.; Tim A. Fischell, Nashville, Tenn.

[73] Assignee: Iso Stent, Inc., Belmont, Calif.

[21] Appl. No.: 604,682

[22] Filed: Feb. 21, 1996

[51] Int. Cl.⁶ .................................................. A61M 29/00
[52] U.S. Cl. .......................................... 606/194; 606/198
[58] Field of Search ................................ 606/198, 191, 606/194, 197, 195, 200; 623/1, 12

[56] References Cited

U.S. PATENT DOCUMENTS

| | | | |
|---|---|---|---|
| 5,342,348 | 8/1994 | Kaplan | 606/198 |
| 5,354,308 | 10/1994 | Simon et al. | 606/198 |
| 5,421,955 | 6/1995 | Lau et al. | 606/198 |

Primary Examiner—Michael Buiz
Assistant Examiner—Kevin Truong

[57] ABSTRACT

The present invention is designed to overcome several disadvantages of prior art balloon expandable stents. Specifically, the Butterfly Expandable To Honeycomb (BETH) stent described herein consists of a collection of circumferential (or vertical) arc structures and diagonal struts. These arcs and struts form a butterfly shape before the stent is expanded and a hexagonal, honeycomb type of structure is created when the stent is fully expanded. Until the nominal stent diameter is reached, the deployed length of the stent is actually longer than the non-deployed length. At the nominal fully-deployed diameter, the deployed stent is exactly the same length as the non-deployed length. This characteristic provides better assurance of completely covering a dilated stenosis as compared to a stent that shortens in length when deployed as is typical of all prior art balloon expandable stents. Furthermore, because at least one quarter of the expanded stent's circumference consist of vertical arcs that are arcs of a circle, they provide the BETH stent with improved radial rigidity.

18 Claims, 4 Drawing Sheets

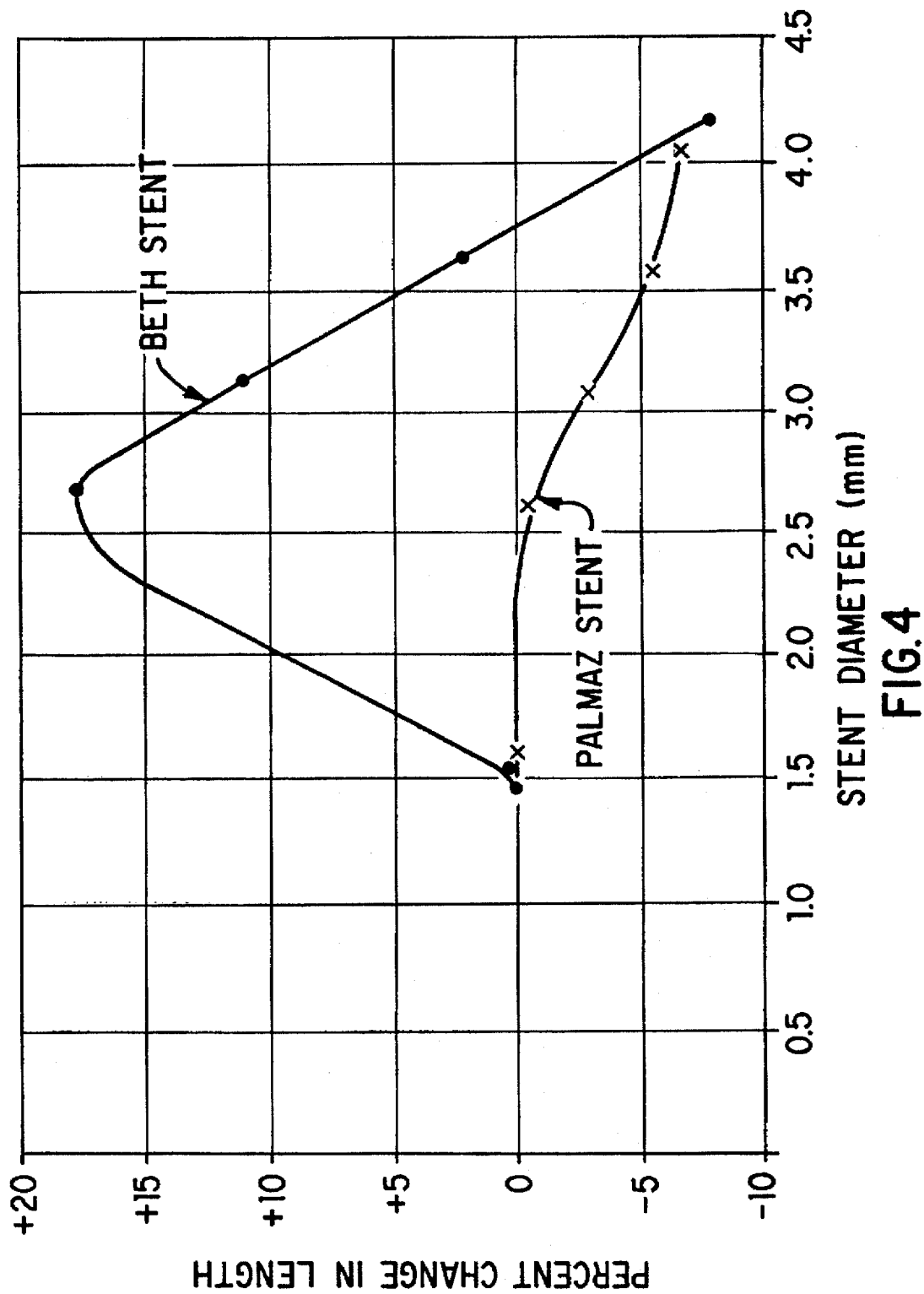

LONGITUDINALLY ELONGATING BALLOON EXPANDABLE STENT

FIELD OF USE

The present invention is an expandable stent insertable into a vessel of a human body for the purpose of creating and maintaining the patency of that vessel.

BACKGROUND OF THE INVENTION

In U.S. Pat. No. 4,739,762, J. C. Palmaz describes a balloon expandable stent that is at its greatest length in its non-deployed state and becomes progressively shorter as it is expanded to progressively greater diameters. This stent shortening can result in incomplete coverage of a dilated stenosis. Furthermore, the Palmaz stent is quite radially elastic which has been shown to cause at least 10% radial recoil after balloon expansion in an artery due to the acute elastic recoil of the artery.

SUMMARY OF THE INVENTION

The present invention is designed to overcome several disadvantages of prior art balloon expandable stents. Specifically, the Butterfly Expandable To Honeycomb (BETH) stent described herein consists of a collection of circumferential (or vertical) arc structures and diagonal struts. These arcs and struts form a butterfly shape before the stent is expanded and a hexagonal, honeycomb type of structure is created when the stent is fully expanded. Until the nominal stent diameter is reached, the deployed length of the stent is actually longer than the non-deployed length. At the nominal fully-deployed diameter, the deployed stent is exactly the same length as the non-deployed length. This characteristic provides better assurance of completely covering a dilated stenosis as compared to a stent that shortens in length when deployed as is typical of all prior art balloon expandable stents. Furthermore, because at least one quarter of the expanded stent's circumference consist of vertical arcs that are arcs of a circle, they provide the BETH stent with improved radial rigidity.

Thus it is an object of this invention to provide a balloon expandable stent that increases in its length as it is expanded radially outward.

Another object of this invention is to provide a balloon expandable stent with improved radial rigidity.

These and other important objects and advantages of this invention will become apparent from the detailed description of the invention and the associated drawings provided herein.

BRIEF DESCRIPTION OF THE DRAWINGS

FIG. 4 is a graph that compares the longitudinal lengthening of the BETH stent as compared to the Palmaz stent described in U.S. patent Ser. No. 4,739,762.

DETAILED DESCRIPTION OF THE INVENTION

Figure 1:
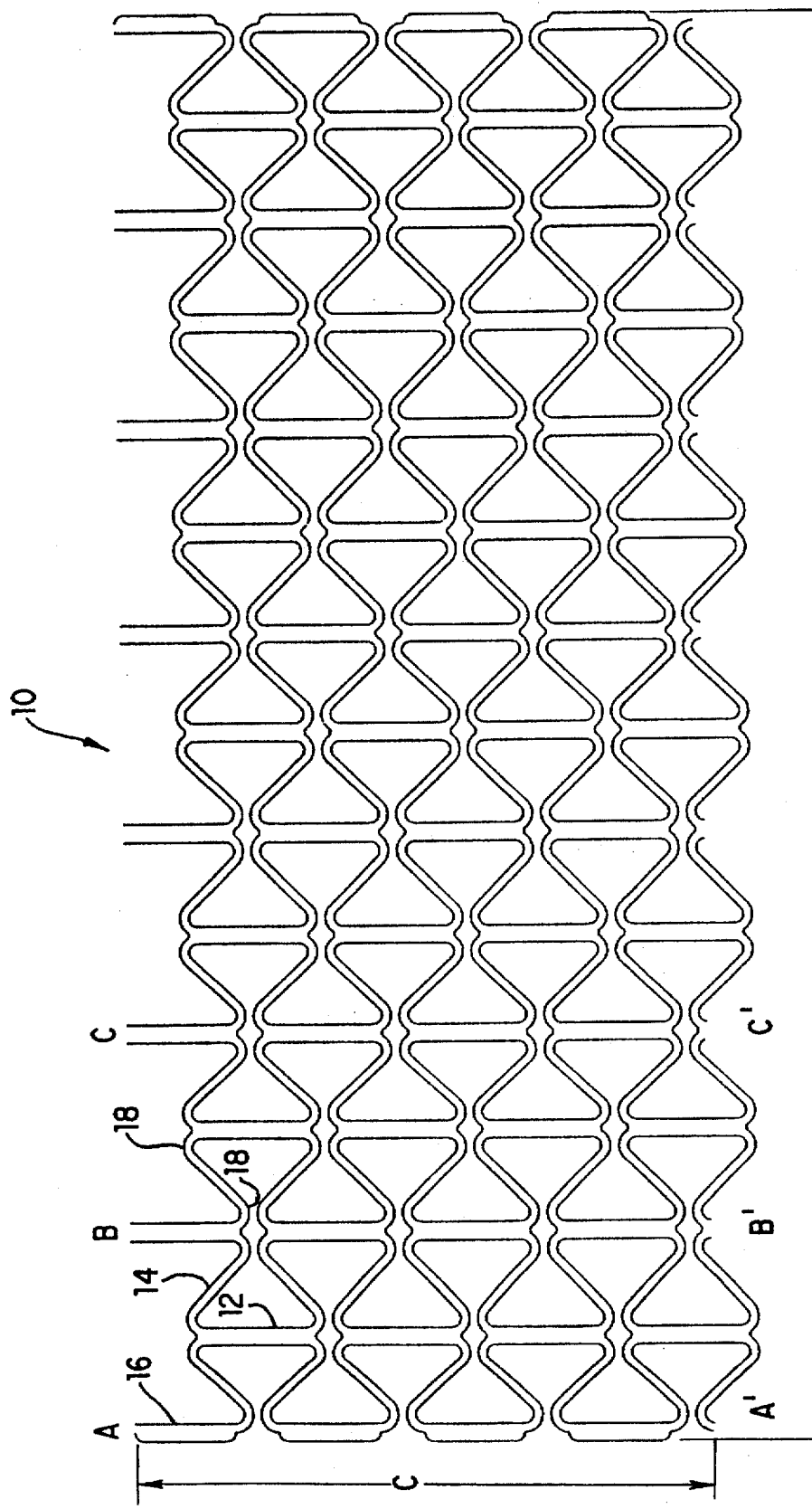
FIG. 1 illustrates the non-deployed BETH stent as it would appear if it were robed out flat to form a 2-dimensional structure.

FIG. 1 illustrates a BETH stent 10 having a non-deployed length "L" and a non-deployed circumference "C". Of course, it should be understood that the stent 10 is in fact in the form of a cylinder (not shown) whose length is "L" and whose diameter is "D" where C=πD. FIG. 1 illustrates the appearance of the surface of the stent 10 if it were cut longitudinally and then out rolled flat into a 2-dimensional structure.

Figure 2:
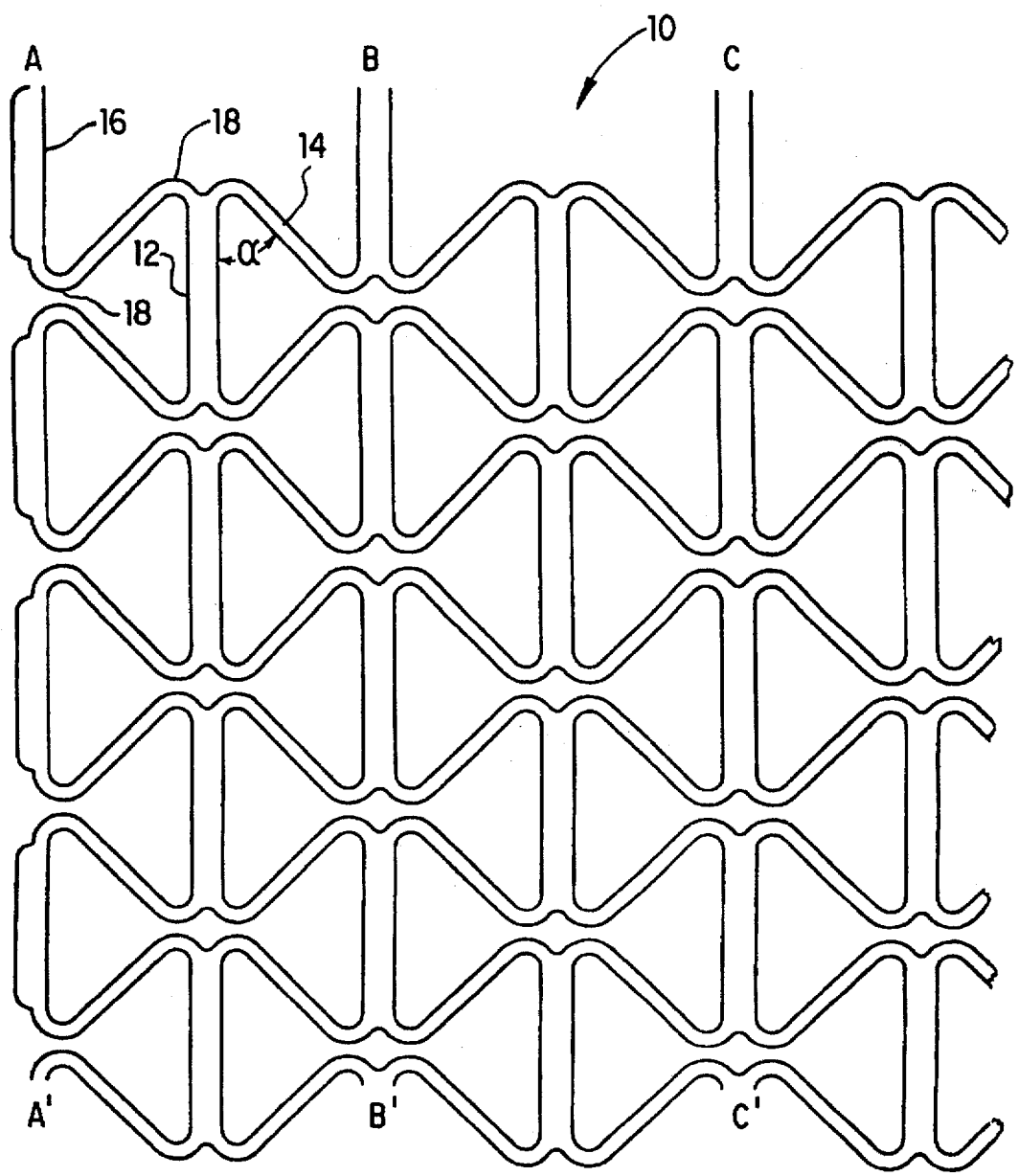
FIG. 2 is an enlarged view of a limited portion of the flat, 2-dimensional non-deployed structure.

FIG. 2 is an enlarged portion of one section of the non-deployed BETH stent 10 shown as a 2-dimensional structure. From both FIGS. 1 and 2 we see that the stent 10 consists of circumferential (or vertical) arcs 12, and diagonal struts 14 and curved sections 18 which collectively have the general form of a butterfly prior to being balloon expanded. The end arcs 16 have a slightly different shape as compared to interior arcs 12. The BETH stent 10 would form a cylinder when the points A, B and C are connected respectively to the points A', B' and C'.

Figure 3:
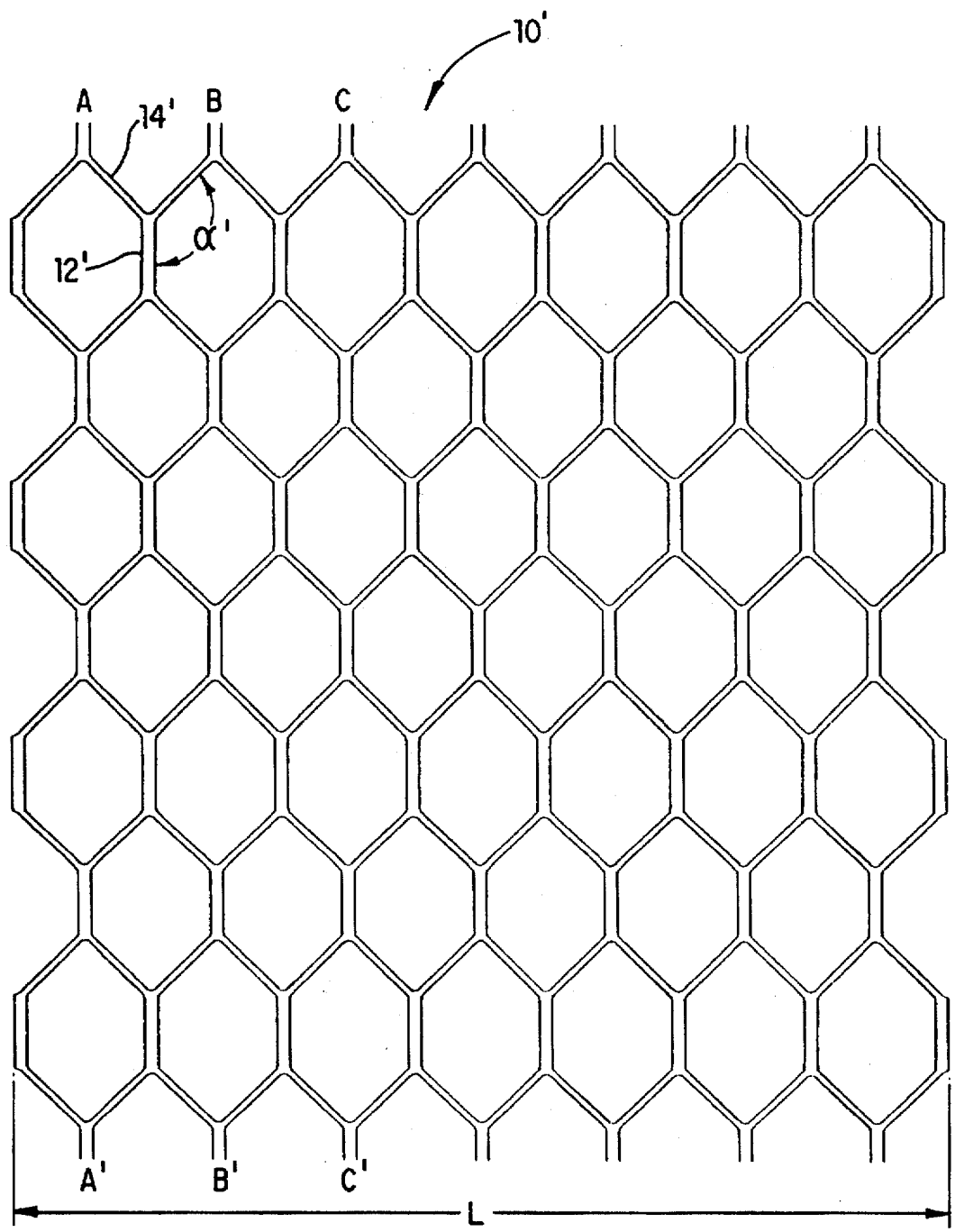
FIG. 3 illustrates the BETH stent as it would appear after deployment if it were rolled out flat to form a 2-dimensional structure.

The cylindrical BETH stent 10 can be placed around a balloon which balloon is located at the distal end portion of a typical balloon angioplasty catheter (not shown). When the balloon is expanded to high pressures (typically 6 to 18 atmospheres), the stent 10 will expand radially out to form the stent 10' as illustrated in FIG. 3. Of course, FIG. 3 illustrates the cylindrical stent 10' as it would appear if it were cut longitudinally and rolled out flat into a 2-dimensional structure.

FIG. 3 illustrates that the deployed BETH stent 10' has become a honeycomb structure that consists of a multiplicity of hexagons that are joined together. After balloon expansion, the shape of the arcs 12' are only trivially different from the arcs 12, and the diagonal struts 14' are essentially identical in shape to the diagonal struts 14, which arcs 12 and diagonal struts 14 are shown in FIGS. 1 and 2. The curved sections 18 are straightened to be generally in alignment with the diagonals 14' as shown in FIG. 3. The angle "α" that lies between the arc 12 and the diagonal strut 14 of FIG. 2 is called the "intersection angle". For the BETH stent design to achieve its objective of increasing in length with increasing diameter, the intersection angle α should lie between 10 and 80 degrees with 45 degrees being a near optimum value. When the stent 10 is radially expanded to form the stent 10', the angle α increases until it becomes the angle α' as shown in FIG. 3. As the angle α increases, the length of the diagonal struts 14 as projected in the longitudinal direction increases thus causing the stent 10 (or 10') to lengthen accordingly. Until the angle 180-α' is less than the angle α, the length L' of the expanded stent 10' will be generally greater than the non-deployed length L of FIG. 1. For example, if α=45 degrees and α'=135 degrees, then the length L≈L'. However, for angles α'<135°, then L'>L, which is an important objective of this stent design. The maximum length of the expanded stent 10' will occur when α'=90 degrees. At α'=180-α, the stent 10 is at its nominal diameter which occurs when L=L'. If the stent 10' is further expanded beyond its nominal diameter, it will start to shorten in length as compared to its pre-deployed length. Some minimum shortening of the stent 10' is acceptable though not desirable.

FIG. 4 is a plot showing the percent change in length of the BETH stent 10 compared to the change in the length of the Palmaz stent. From the curve for the BETH stent 10, it is clear to see that L' is greater than L for stent diameters up to the nominal stent diameter of 3.75 mm which lengthening is an important objective of this invention.

FIG. 3 shows that the deployed stent 10' consists of a multiplicity of arcs 12' all of which are in fact arcs of circles which, if completed for 360 degrees would maximize the stent's radial rigidity. Because the deployed stent 10' has a multiplicity of hexagons, it does in fact provide a honeycomb type of structure that exhibits a high degree of radial rigidity as compared to many other stents such as the Palmaz stent described in U.S. Pat. No. 4,739,762.

Although the arcs 12 and diagonals 14 could have the same width, as shown in FIGS. 1, 2 and 3, improved longitudinal flexibility of the pre-deployed stent 10 (and the deployed stent 10') is achieved when the width of the diagonals 14 is considerably smaller than the width of the arcs 12. For example, the width of the arcs 12 would typically be twice the width of the diagonal struts 14. What is most important is that the curved sections 18 of FIG. 2 are narrower than the arcs 12. It is envisioned that the diagonal struts 12 could be considerably wider as compared to the curved sections 18.

Typical dimensions of the non-deployed stent 10 would be between 1 and 3 mm in diameter and between 10 and 100 mm in length. Typical width of a vertical arc 12 would be between 0.08 and 0.3 min. Typical width of a diagonal strut 14 would be between 0.05 and 0.2 mm. Typical width of a curved section 18 would be between 0.04 ansd 0.1 min. Typical materials for the BETH stent would be stainless steel, titanium, tantalum, Nitinol or any other material known to be biocompatable and have the appropriate physical characteristics for forming a balloon expandaisle or self-expanding stent. It is further envisioned that BETH stent could be plated with a radiopaque metal such as gold or an anti-thrombogenic coating such as heparin could be applied. Furthermore, the BETH stent is conceived to include a radioisotope for the prevention of neointimal hyperplasia as described in U.S. Pat. No. 5,059,166, which patent is included herein by reference. When used as a platform for a radioisotope, the BETH stent has two advantages over prior art designs. These are (1) the regular hexagon shape minimizes dose hot spots and (2) the steep negative slope of the length vs diameter curve shown in FIG. 4 causes a radioisotope BETH stent to provide greater uniformity of tissue dose over a large range of diameters as compared to the Palmaz-Schatz stent.

Although the use of the stent is described with particular reference to implantation in arteries, it should be understood that the BETH stent is suitable for implantation in any vessel of the human body that is able to be stented.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A cylindrical stent for placement in a vessel of a human body, the stent having a longitudinal axis and also having circumferential arcs and diagonal struts with the intersection angle between the circumferential arcs and the diagonal struts being within the range of 10 to 80 degrees when the stent is in its non-deployed state, the diagonal struts being joined by curved sections to the circumferential arcs which collectively form a closed perimeter cell, the closed perimeter cell having two parallel, circumferential arcs located at the longitudinal extremities of the closed perimeter cell and the circumferential arcs lying generally perpendicular to the stent's longitudinal axis.

2. The stent of claim 1 wherein the width of the circumferential arcs is greater than the width of the diagonal struts.

3. The stent of claim 1 wherein the stent is formed from stainless steel.

4. The stent of claim 1 wherein the stent is formed from tantalum.

5. The stent of claim 1 wherein the stent is constructed of a metal that is coated with a high density, radiopaque metal.

6. The stent of claim 5 wherein the metal is gold.

7. The stent of claim 1 wherein the stent is coated with an anti-thrombogenic coating.

8. The stent of claim 1 wherein the stent includes a radioisotope material to prevent neointimal hyperplasia subsequent to balloon angioplasty.

9. A cylindrical stent for implantation into a vessel of a human body, the stent being adapted to lengthen longitudinally as its diameter increases from its non-deployed diameter, the stent structure to accomplish lengthening including a multiplicity of closed perimeter cells each cell including within its perimeter at least two diagonal struts, which diagonal struts increase their projected length in the longitudinal direction as the stent diameter is increased from its non-deployed diameter.

10. The stent of claim 9 wherein the stent is constructed of a metal that is coated with a high density, radiopaque metal.

11. The stent of claim 10 wherein the metal is gold.

12. The stent of claim 9 wherein the stent is coated with an anti-thrombogenic coating.

13. The stent of claim 9 wherein the stent includes a radioisotope material to prevent neointimal hyperplasia subsequent to balloon angioplasty.

14. A stent in the form of a thin-walled cylinder having a longitudinal axis, the stent having a multiplicity of hexagonal cells that form a honeycomb type cylindrical structure, each side of each hexagonal cell being approximately equal in length to every other side and each hexagonal cell having a first circumferential arc located at one longitudinal extremity of the hexagonal cell and a second circumferential arc located at the opposite longitudinal extremity of the hexagonal cell, the first and second circumferential arcs being generally parallel to each other and each circumferential arc lying generally perpendicular to the stent's longitudinal axis.

15. The stent of claim 14 wherein the width of the circumferential arcs is greater than the width of the diagonal struts.

16. The stent of claim 14 wherein the stent has curved sections that join the circumferential arcs to the diagonal struts.

17. The stent of claim 16 wherein the curved sections have a narrower width as compared to the diagonal struts.

18. The stent of claim 14 wherein the stent includes a radioisotope material to prevent neointimal hyperplasia subsequent to balloon angioplasty.

* * * * *